United States Patent [19]
Howell et al.

[11] Patent Number: 5,674,224
[45] Date of Patent: Oct. 7, 1997

[54] BONE MULCH SCREW ASSEMBLY FOR ENDOSTEAL FIXATION OF SOFT TISSUE GRAFTS AND METHOD FOR USING SAME

[76] Inventors: Stephen M. Howell, 4834 Roselin Way, Elk Grove, Calif. 95759; Roy Carl Wiley, 73 S. C.R. 325, E. Warsaw, Ind. 46580

[21] Appl. No.: 342,324

[22] Filed: Nov. 18, 1994

[51] Int. Cl.⁶ ............................................. A61B 17/58
[52] U.S. Cl. .............................. 606/88; 606/86; 606/89; 606/72
[58] Field of Search ..................... 606/62, 63, 64, 606/65, 66, 67, 68, 72, 73, 92, 93, 94, 86, 87, 88, 89

[56] References Cited

U.S. PATENT DOCUMENTS

| | | | |
|---|---|---|---|
| 324,768 | 8/1885 | Hunt | 606/72 |
| 2,382,019 | 8/1945 | Miller | 606/72 |
| 3,374,786 | 3/1968 | Callender, Jr. . | |
| 4,059,102 | 11/1977 | Devas . | |
| 4,407,793 | 10/1983 | Akimova et al. | 424/81 |
| 4,708,132 | 11/1987 | Silvestrini . | |
| 4,751,921 | 6/1988 | Park | 606/93 |
| 4,870,957 | 10/1989 | Goble et al. . | |
| 4,922,897 | 5/1990 | Sapega et al. . | |
| 4,927,421 | 5/1990 | Goble et al. . | |
| 5,019,079 | 5/1991 | Ross . | |
| 5,084,050 | 1/1992 | Draenert . | |
| 5,102,414 | 4/1992 | Kirsch . | |
| 5,116,337 | 5/1992 | Johnson . | |
| 5,129,902 | 7/1992 | Goble et al. . | |
| 5,151,104 | 9/1992 | Kenna . | |
| 5,152,790 | 10/1992 | Rosenberg et al. . | |
| 5,156,616 | 10/1992 | Meadows et al. | 606/73 |
| 5,209,753 | 5/1993 | Biedermann et al. . | |
| 5,217,462 | 6/1993 | Asnis et al. . | |
| 5,234,430 | 8/1993 | Huebner . | |
| 5,246,441 | 9/1993 | Ross et al. . | |
| 5,266,075 | 11/1993 | Clark et al. . | |
| 5,268,001 | 12/1993 | Nicholson et al. . | |
| 5,314,476 | 5/1994 | Prewett et al. | 623/16 |
| 5,320,115 | 6/1994 | Kenna . | |
| 5,320,626 | 6/1994 | Schmieding . | |
| 5,393,302 | 2/1995 | Clark et al. . | |
| 5,431,655 | 7/1995 | Melker et al. | 606/79 |

FOREIGN PATENT DOCUMENTS

| | | |
|---|---|---|
| 408416A1 | 1/1991 | France . |
| WO 92/02196 | 2/1992 | WIPO . |

OTHER PUBLICATIONS

"Ligament Screw System" (©1992 Arthrotek, Inc.).

Primary Examiner—Michael Buiz
Assistant Examiner—Mark S. Leonardo
Attorney, Agent, or Firm—Harness, Dickey & Pierce, P.L.C.

[57] ABSTRACT

An apparatus and a method for providing initial mechanical fixation of a hamstring graft and subsequent biologic bonding of the graft to the walls of a femoral tunnel. The apparatus includes a two-part screw assembly that is introduced through the lateral femoral condyle. The two-part screw assembly includes an outer screw and an inner screw. The outer screw includes a threaded body and an outwardly-extending nose portion that is of a diameter reduced from the threaded body. The nose portion provides a mechanical fixation point by functioning as a post within the femoral tunnel. A hamstring graft is looped around this post, mechanically fixing one end of the graft. Bone reamings, or mulch, is inserted using a bone graft impactor tool through a hollow throughbore axially defined within the body of the outer screw. The throughbore is in communication with an opening adjacent the nose portion and the mulch is deposited into the femoral tunnel around the tendon loop. The inner screw is inserted into the throughbore.

18 Claims, 7 Drawing Sheets

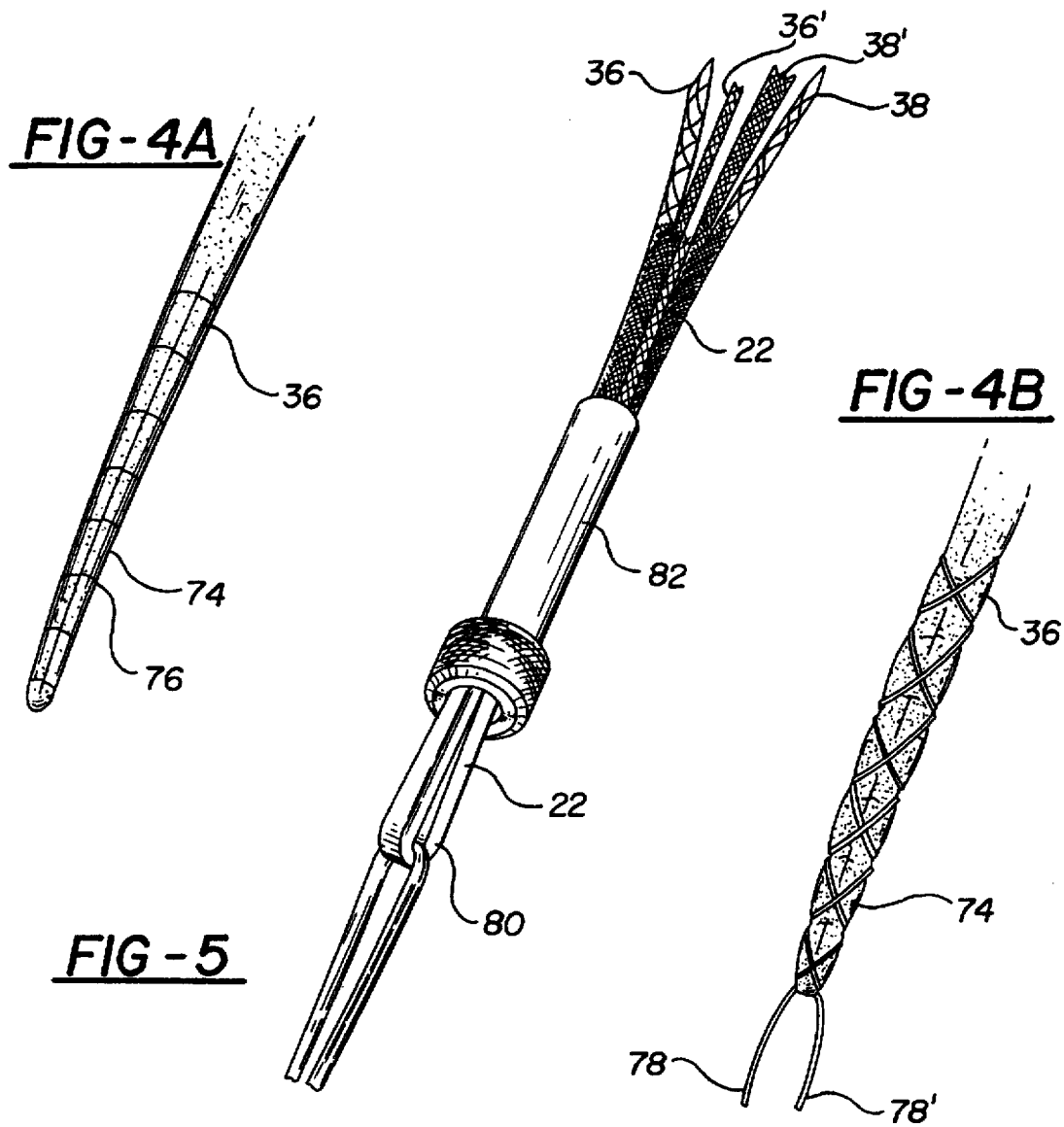
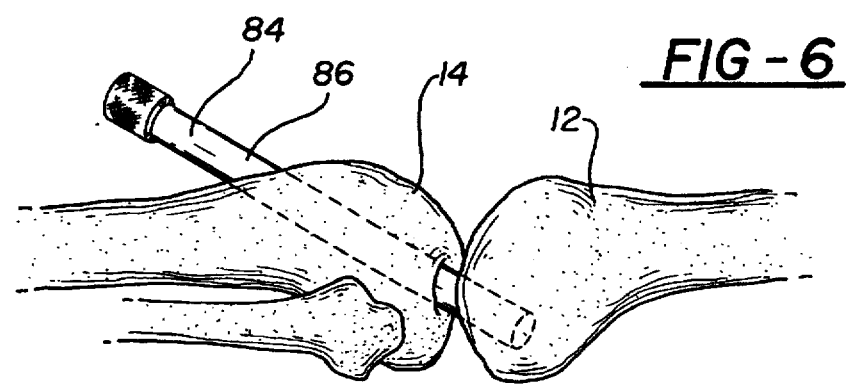

BONE MULCH SCREW ASSEMBLY FOR ENDOSTEAL FIXATION OF SOFT TISSUE GRAFTS AND METHOD FOR USING SAME

BACKGROUND OF THE INVENTION

The present invention relates to endoscopic graft fixation. More particularly, the present invention relates to an apparatus and a method to reconstruct the anterior cruciate ligament with hamstring or fascia lata grafts within the femoral tunnel while providing a bone mulch environment for graft incorporation.

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

Currently, fascia lata grafts are sutured to a threaded stud and turned into the femoral tunnel. Unfortunately, this procedure can result in the graft being wrapped upon itself during insertion. Hamstring grafts are currently fixed over a screw in the tibial tunnel and fixed on the lateral femur. This technique requires the femoral tunnel to completely penetrate the femur. In addition, according to present procedures, fixation of the graft on the femoral side requires a large incision.

Attempts have been made to improve known techniques. Such attempts are embodied in exemplary patents including: U.S. Pat. No. 4,922,897, issued May 8, 1990, to Sapega et al. for Apparatus And Method For Reconstructive Surgery; U.S. Pat. No. 4,927,421, issued May 22, 1990, to Goble et al. for Process Of Endosteal Fixation Of Ligament; U.S. Pat. No. 5,129,902, issued Jul. 14, 1992, to Goble et al. for Endosteal Ligament Retainer And Process; and U.S. Pat. No. 5,320,115, issued Jun. 14, 1994, to Kenna for Method And Apparatus For Arthroscopic Knee Surgery.

In addition, attempts have been made at improving anchoring systems for ligaments grafts. Such efforts are embodied in exemplary patents including: U.S. Pat. No. 4,870,957, issued Oct. 3, 1989, to Goble et al. for Ligament Anchor System; U.S. Pat. No. 5,116,337, issued May 26, 1992, to Johnson for Fixation Screw And Method For Ligament Reconstruction; and U.S. Pat. No. 5,152,790, issued Oct. 6, 1992, to Rosenberg et al. for Ligament Reconstruction Graft Anchor Apparatus.

However, while offering certain improvement in arthroscopic surgery to repair ligaments, these patents still fail to overcome the limitations on endoscopic hamstring graft fixation due in, in many instances, to the weakness of the suture used to span the gap between the tendon graft and the fixation post. Known fixation techniques have forced surgeons using hamstring graft to avoid aggressive rehabilitation. Accordingly, a method to mechanically fix and to allow for a biologic bond of a hamstring graft directly to the walls of a femoral tunnel is needed.

SUMMARY OF THE PRESENT INVENTION

An advantage of the present invention is to provide an apparatus and a method that provides secure initial mechanical fixation of a hamstring graft.

A further advantage of the present invention is to provide an apparatus and a method that allows for a biologic bond of the hamstring graft directly to the walls of a femoral tunnel.

Another advantage of the present invention is to provide such an apparatus and a method that may be used conveniently and reliably.

A further advantage of the present invention is to provide an apparatus and method that allows for insertion of a graft that permits the use of smaller incisions.

Yet another advantage of the present invention is to provide an apparatus and method for allowing biological bond of a hamstring graft to occur.

The present invention utilizes a two-part screw assembly that is introduced through the lateral femoral condyle. The two-part screw assembly includes an outer screw and an inner screw. The outer screw includes a threaded body and an outwardly-extending nose portion that is of a diameter reduced from the threaded body. The nose portion provides a mechanical fixation point by functioning as a post within the femoral tunnel. A hamstring graft is looped around this post, mechanically fixing one end of the graft.

Fixation is further enhanced biologically by inserting bone reamings, or mulch, through a hollow throughbore axially defined within the body of the outer screw. The throughbore is in communication with an opening adjacent the nose portion. The bone mulch is first delivered into the throughbore and is driven through the center of the outer screw and into the femoral blind bore by a bone graft impactor tool. Voids between the inner walls of the femoral tunnel and the tendon graft are tightly packed with bone graft.

The screw assembly of the present invention achieves two fundamental objectives. First, it provides a method by which the bone graft may be initially mechanically fixed. Second, it augments the long-term bond between the tendon graft and a bone tunnel interface by providing a fertile environment for expedited reattachment of the graft to the inner walls of the blind bore to occur.

Accordingly, the present invention overcomes the known problems commonly associated with arthroscopic surgery for repair of the anterior cruciate ligament.

Other advantages and features of the present invention will become more apparent from the following detailed description when read in conjunction with the accompanying drawings.

BRIEF DESCRIPTION OF THE DRAWINGS

Various advantages of the present invention will become apparent to one skilled in the art upon reading the following specification and by reference to the following drawings in which:

FIG. 4a is a partial view illustrating muscle end of the hamstring that has been tapered and wrapped transversely with suture;

FIG. 4b is a view similar to that of FIG. 4a but illustrating the tapered muscle end of the tendon with a whip stitch suture overlapping the transverse suture;

FIG. 5 is a perspective view illustrating a prepared graft assembly within a sizing sleeve;

FIG. 6 is a perspective view illustrating the tibia and the femur with an impingement rod disposed through the tibial tunnel;

3

Figure 8:
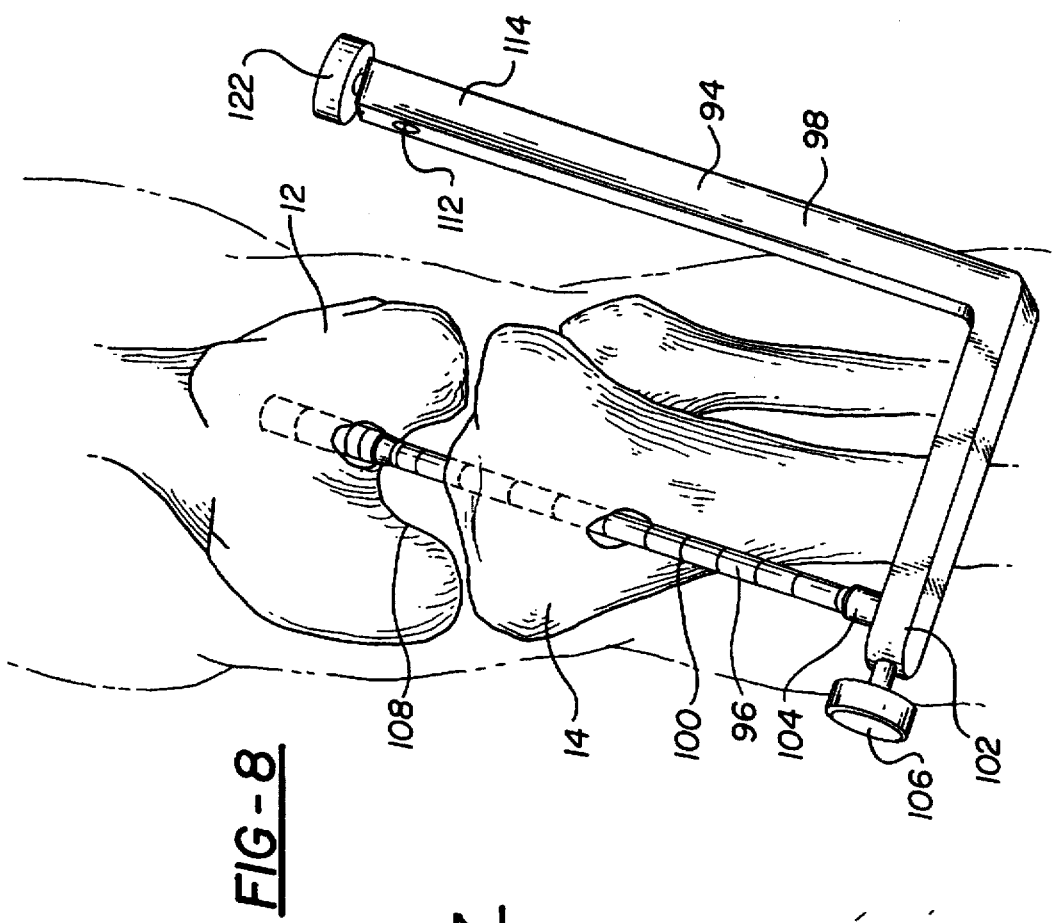
Figure 7:
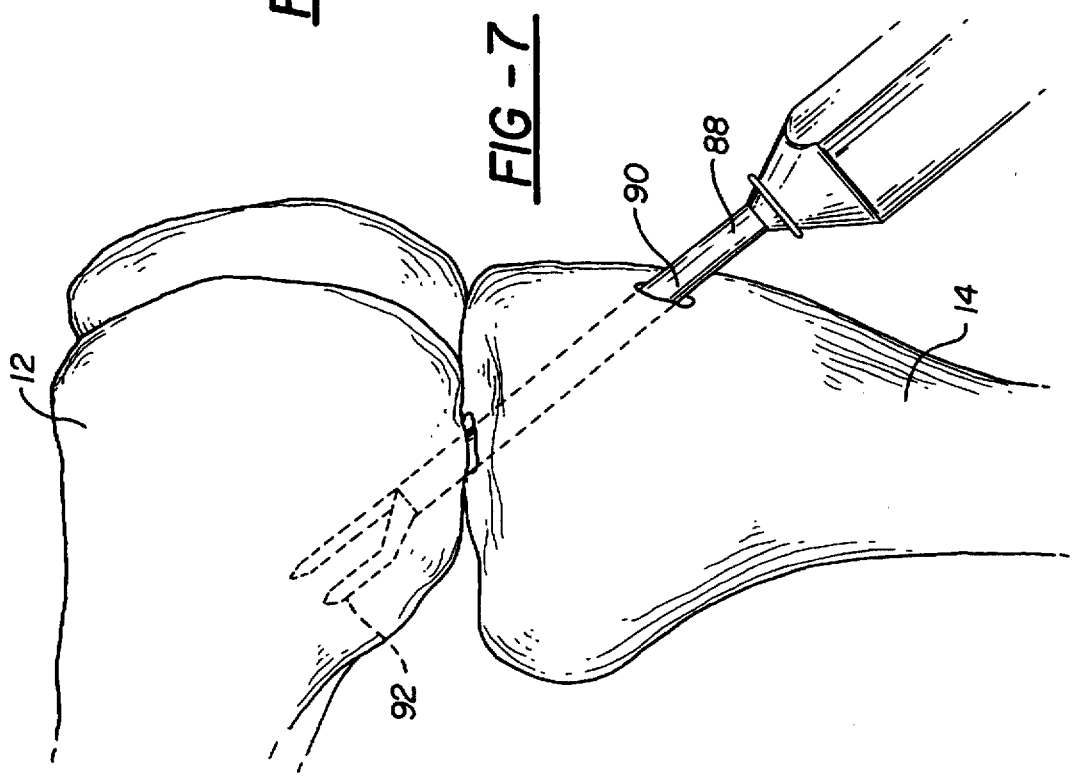
Figure 10:
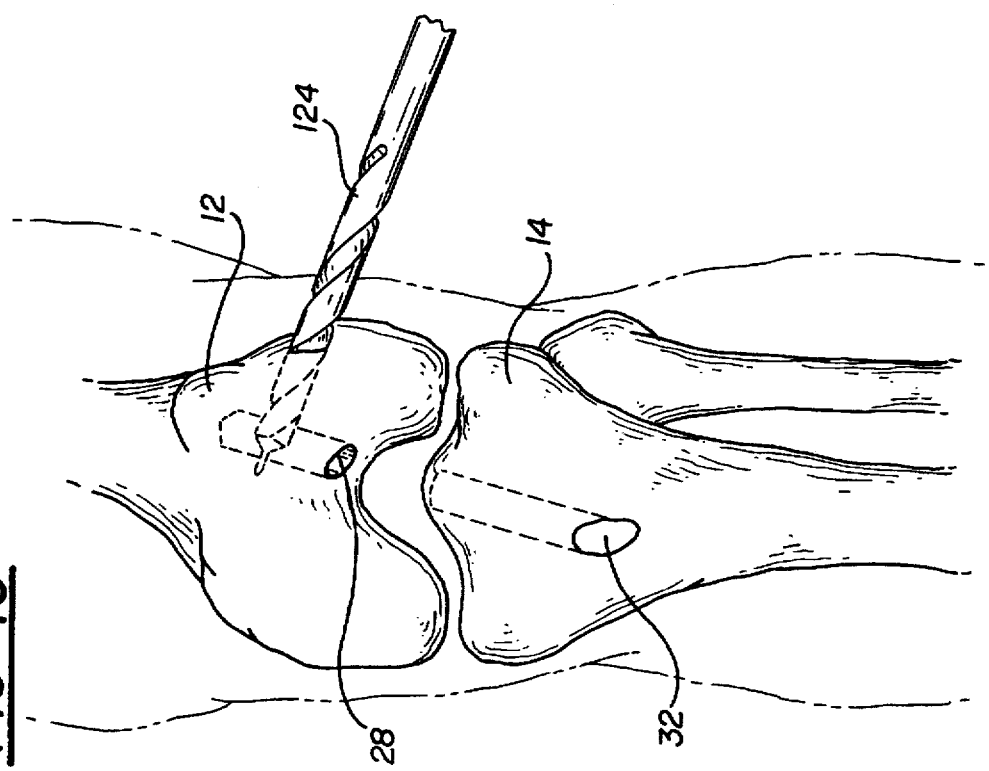
Figure 9:
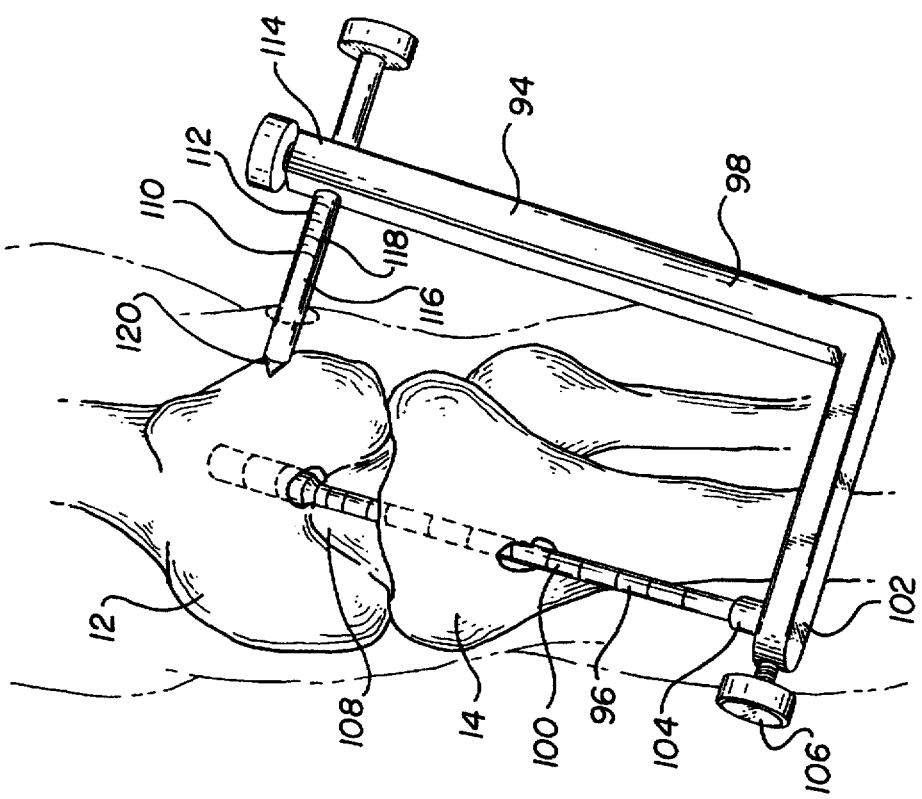
Figure 12:
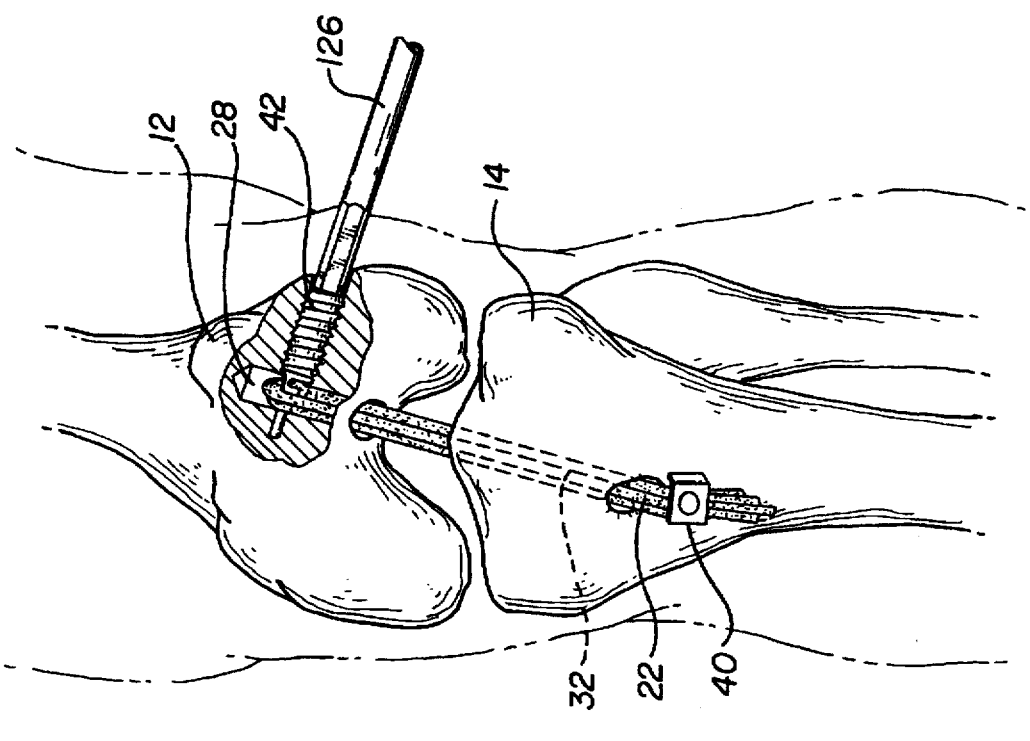
Figure 11:
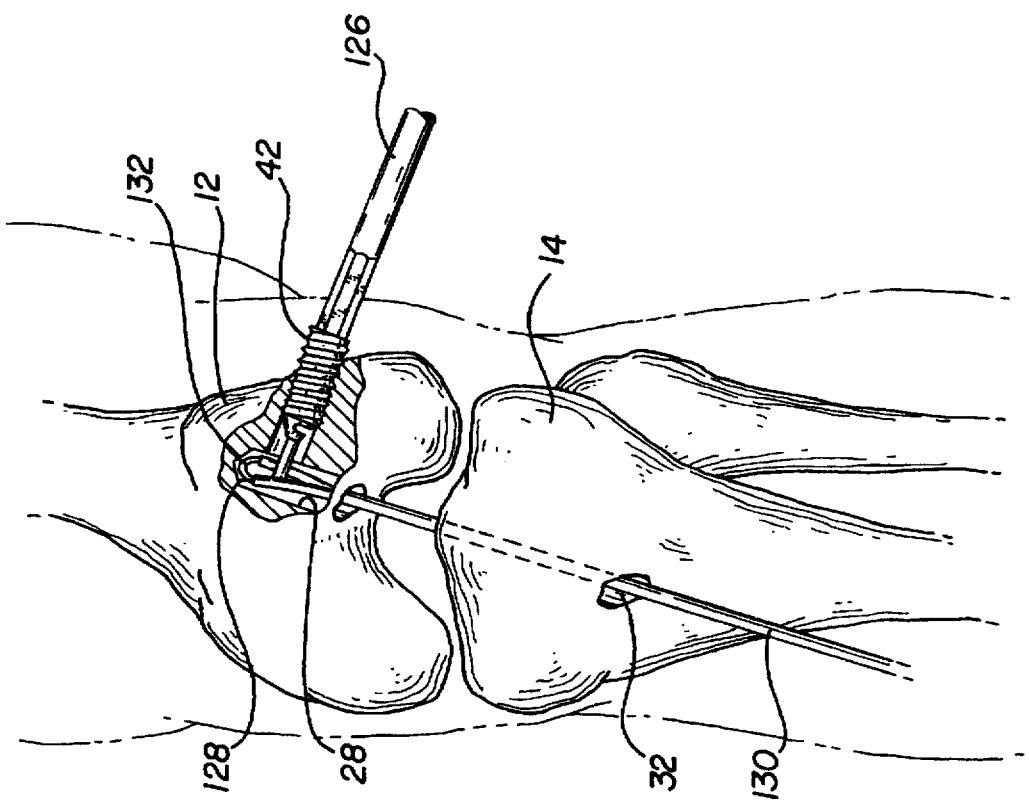
Figure 13:
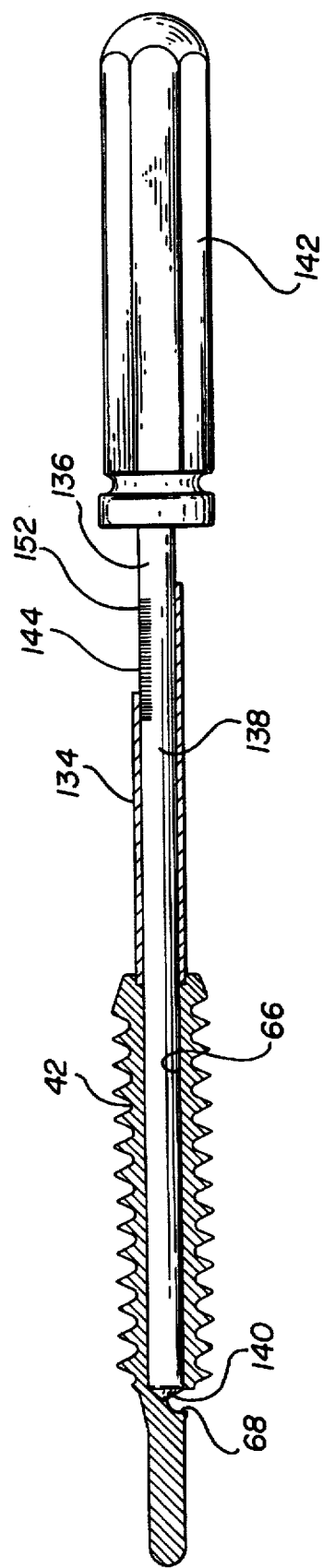
Figure 14:
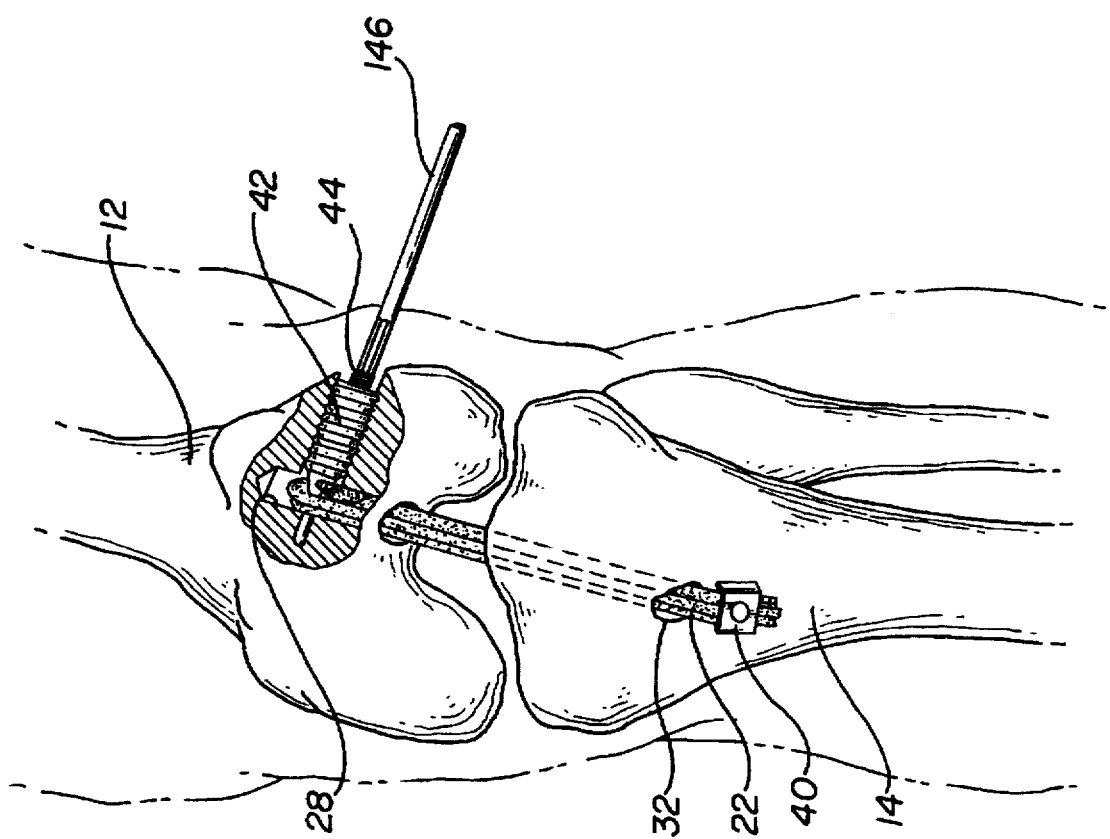

FIG. 7 is a side view of a flexed knee with an endoscopic femoral aimer in place through the tibial tunnel and having its tip in place resting against the intercondylar notch;

FIG. 8 is an anterior deep view of the left knee joint illustrating the drill guide in place;

FIG. 9 is a view similar to that of FIG. 8 but showing an aiming bullet attached to the drill guide;

FIG. 10 is a view similar to that of FIG. 9 showing the drill guide removed and a reamer in place of the aiming bullet;

FIG. 11 is a view similar to that of FIG. 10 showing the reamer removed and the outer screw in place within a transverse bore defined in the femur and a suture passing device positioned within the tibial tunnel and the femoral tunnel;

FIG. 12 is a view similar to that of FIG. 11 with the graft assembly in place and fastened to the tibia;

FIG. 13 is a sectional view of the bone graft impactor in place within the outer screw and a bone graft delivery sleeve; and FIG. 14 is a view similar to that of FIG. 12 showing the inner screw being fitted into the outer screw.

DETAILED DESCRIPTION OF THE PREFERRED EMBODIMENT

The following discussion of the preferred embodiment of the present invention is merely exemplary in nature and is in no way intended to limit the invention or its application or uses.

Figure 1:
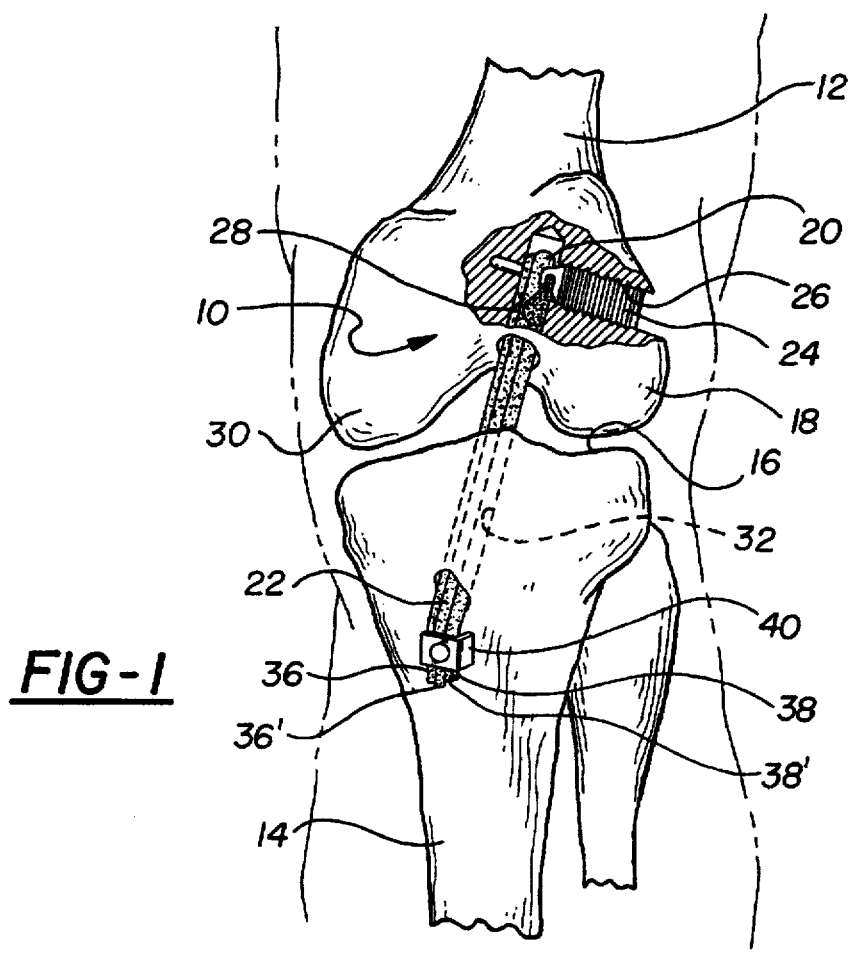
FIG. 1 is an anterior deep view of the left knee joint illustrating the endosteal fixation system of the present invention.

Referring to FIG. 1, an anterior deep view of a left knee is shown illustrating the positioning and securing of a tendon graft in accordance with the graft replacement system, generally illustrated by the number 10, of the preferred embodiment of the present invention. The graft replacement system 10 is designed for use between a femur 12 and a tibia 14. More particularly, the present system is directed to reconstruction of the anterior cruciate ligament (not shown). The anterior cruciate ligament extends obliquely, superiorly, and posteriorly from its origin on the anterior intercondylar eminence 16 of the tibia 14 continuing to the medial side of the lateral femoral condyle 18. Of course, while the graft replacement system 10 is shown in conjunction with the left knee joint, the graft replacement system 10 could as well be used for ligament grafting in the right knee joint.

According to the graft replacement system 10 of the present invention, a looped end 20 of a tendon graft bundle 22 is retained by a two-part screw assembly 24 (described below) which is positioned within a transverse femoral tunnel 26 defined in the femur 12. The looped end 20 is disposed in an axial femoral tunnel 28 defined in the femur 12 substantially between the medial and lateral condyles 30 and 18 respectively. In addition, the tendon graft bundle 22 is positioned through a tibial tunnel 32. A quartet of graft ends, generally labeled as 34, is composed of pair of semitendinosus tendon ends 36, 36' and a pair of gracilis tendon ends 38, 38'. The quartet of graft ends 34 extends out of the lower end of the tibial tunnel 32 and are fastened to the tibia 14 by a fastener 40. The fastener 40 may be of any type known such as surgical staples or a fixation screw and washer system.

Figure 2:
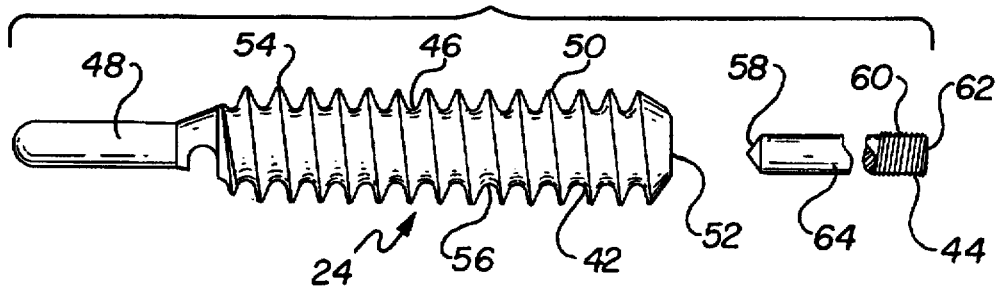
FIG. 2 is an exploded view of the inner and outer screws comprising the screw assembly of the present fixation system.

With reference to FIG. 2, the two-part screw assembly 24 is illustrated in an exploded view. The screw assembly 24 includes an outer screw 42 and an inner screw 44. Both the outer screw 42 and the inner screw 44 are preferably composed of the same material such as Ti-6Al-4V, or a similar biocompatible material. The outer screw 42 comprises a body 46 having a smooth ligament holding nose 48, an intermediate threaded portion 50, and an inner screw receiving end 52. The threaded portion 50 includes screw threads 54 formed on a shank 56. The threads 54 are preferably of the right-hand type and are preferably self-tapping. Overall, the thread and size profile of the threaded portion 50 is similar to that of an interference screw.

The nose 48 is of a reduced diameter relative to the diameter of the threaded portion 50. The inner screw receiving end 52 is preferably a hex (not shown) so as to receive the working end of a screwdriver (shown below in FIG. 11 and discussed in relation thereto). The overall length of the outer screw 42 is preferably between 20 mm and 35 mm excluding the 12 mm length of the nose, while the diameter preferably ranges between approximately 2.5 mm at the nose 48 and approximately 10.5 mm at the threaded portion 50.

The inner screw 44 of the screw assembly 24 is preferably solid and includes a conical, mulch-driving end 58, a threaded intermediate portion 60, and a screw driver-receiving end 62. The intermediate portion 60 has external threads 64 formed thereon. Like the end 52 of the outer screw 42, the screw driver-receiving end 62 is preferably hex (not shown) so as to receive the driving end of a screw driver (shown below in FIG. 14 and discussed in relation thereto).

Figure 3:
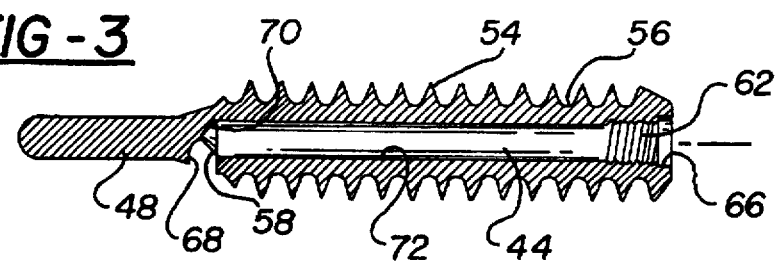
FIG. 3 is a sectional view of the inner and outer screws of FIG. 2 with the inner screw in place within the throughbore of the hollow outer screw.

The inner screw 44 preferably has an outer diameter of approximately 5.0 mm with a 6.5 mm threaded portion (i.e., ¼×20 left hand thread) and is adapted for insertion into a longitudinal bore 66 axially defined within the intermediate threaded portion as illustrated in FIG. 3. The bore 66 is illustrated as being defined between the end 52 terminating adjacent the nose 48 at an opening 68 defined at one side of the outer screw 42. A seat 70 defining a concave cone formed to mate with the conical end 58 of the inner screw 44 provides a forward end wall of the bore 66. Internal threads 72 extend approximately 5–10 mm from a region approximately 3–4 mm from the open end of the bore 66 and drop down to a smooth shank. The inner screw 44 is adjustably threaded within the bore 66, as will be described below.

The principal steps for using the graft replacement system 10 and the installation of the screw assembly 24 are shown in FIGS. 4a through 12 and 14 and are discussed in relation thereto.

The initial step of grafting of the hamstring according to the present system is to prepare the hamstring graft. As noted above, two side-by-side tendons compose the graft bundle 22—a semitendinosus tendon and a gracilis tendon. One end of each of these tendons must be prepared for looping over the nose 48. With respect first to FIG. 4a, an illustration of one end of one of the tendons is shown being prepared. It must be understood that this illustration applies to both the semitendinosus tendon and the gracilis tendon.

The tendons are first harvested from semitendinosus and gracilis muscle by known techniques. The harvested tendons are prepared to facilitate passage of the graft bundle 22 through the tunnels 32 and 28, defined in the femur 12 and tibia 14 respectively as will be described below. Such preparation includes trimming of the tissue so that the two ends 36 and 38 taper from their midpoints to the muscle or origin ends 74, rolling this section and suturing it both transversely and axially with a running absorbable suture 76 as shown in FIG. 4a. The tapering of the ends 36 and 38 of the graft bundle 22 minimizes difficulty in passing the graft bundle 22 through the bores in the bones.

FIG. 4b illustrates how the taper is further secured by encircling the broader, periosteal or insertion end of each graft with an absorbable suture using a whip stitch. Encircling of the ends 36 and 38 of the graft bundle 22 with suture prevents bunching when tension is applied to pull the muscle end of the graft through the tunnels. The whip stitch results in a pair of sutures 78, 78' being suspended from the end 74. Similar tapering and suturing is also done to one end of the other tendon.

The midsections of the paired tendons are next looped over an umbilical tape 80 to form the graft bundle 22 (having four ends—two paired tapered and bound ends 36 and 38 and two untapered and unbound ends 36' and 38'). Alternatively, it would be appreciated that the ends 36' and 38' may be bound. The umbilical tape 80 and the graft bundle 22 is next pulled through a series of sizing sleeves, only one of which is shown as sleeve 82 in FIG. 5. The diameter of the smallest sizing sleeve that can be freely passed over the graft bundle 22 is used to select a drill for reaming the tibial tunnel 32 and the femoral tunnel 28 as described below. The prepared bundle graft 22 is set aside for later insertion.

The preparation of the bundle graft 22 thus completed, preparation of the femur 12 and the tibia 14 begins. The tibial tunnel 32 is first drilled. The location of the tibial tunnel 32 is customized for variability in roof angle and knee extension by using an impingement free tibial drill guide system available from Arthrotek and then subsequently verified using impingement rod 84 as illustrated in FIG. 6 and as known to those skilled in the art. Other tibial drill guide systems may be used. The rod 84 comprises an elongated body 86. The intercondylar notch is next expanded using known techniques, and the impingement rod 84 is passed into the intercondylar notch through the tibial tunnel 32 with the knee fully extended. This latter procedure is done to confirm that roof impingement is fully eliminated.

With reference to the next step that is illustrated in FIG. 7 showing the impingement rod 84 removed, the knee is positioned in approximately 40–50 degrees of flexion, and a femoral aimer 88, such as Model No. 909627 produced and distributed by Arthrotek, is inserted into the tibial tunnel 32. The aimer 88 includes an elongated body 90 and a tip 92. As illustrated, the aimer 88 is positioned so that the tip 92 is placed in the intercondylar notch in the over-the-top position. The knee is then allowed to fully flex once the aimer 88 is positioned, thus ensuring its proper seating. A cannulated cutting reamer (not shown) is used next to prepare the femoral tunnel 28. The femoral tunnel 28 is oriented at the 11:00 position for the right knee and at the 1:00 position for the left knee. The tunnel 16 is drilled approximately 25 mm in length using an endoscopic reamer. Deeper drilling of the tunnel 16 is eliminated as is drilling beyond the cortex.

With reference next to FIG. 8, after the tibial tunnel 32 and the femoral tunnel 28 have been prepared, the knee is flexed from between 70 to 90 degrees. A U-shaped drill guide 94 is shown in position between the femur 12 and the tibia 14. The drill guide comprises a removable insertion rod 96 and an outrigger 98. The insertion rod 96 includes a plurality of markings 100 peripherally defined along its length. A particular insertion rod 96 is selected so as to match the diameter of the femoral tunnel 28. The outrigger 98 includes an insertion rod attachment end 102 having an insertion rod receptacle 104.

The insertion rod 96, once selected, is positioned within the insertion rod receptacle 104 and is secured therein by rotated adjustment of a knob 106. The outrigger 98 is then positioned on the lateral side of the knee. The insertion rod 96 is inserted through the tibial tunnel 32, the intercondylar notch 108 and approximately 25 mm into the femoral tunnel 28. The depth of insertion of the rod 96 is verified visually by observation of the markings 100 so that the rod 96 is inserted no more than 25 mm inside the femoral tunnel 28.

Thereafter, and with reference to FIG. 9, an aiming bullet 110 is inserted through an aperture 112 defined in a bullet support end 114 of the outrigger 98. The aiming bullet 110 comprises an elongated body 116 having a series of adjacent peripheral adjustment markings 118. The body 116 terminates at a tip 120. The bullet 110 is held in position with respect to the outrigger 98 by an adjustment knob 122.

With the bullet 110 in place, the drill guide 94 is rotated so that the tip 120 of the bullet 110 touches the skin anterior to the origin of the lateral collateral ligament (not shown). Once the drill guide 94 is so positioned, the skin is marked where the tip 120 contacts the skin. At that point an approximately 15 mm—long incision is made directly to the bone through the skin, the iliotibial band (not shown), and the capsule (again not shown).

Still with reference to FIG. 9, once the incision is made, the bullet 110 is twisted through the incision until it rests against the bone as illustrated. The surgeon thereafter removes his hands from the drill guide 94 and the knob 122 is tightened against the bullet 110 to secure the tip 120 against the bone.

The markings 118 imprinted on the body 116 of the bullet 110 are used to determine the length of the outer screw 32. The markings 118 are read from the side of the bullet support end 114 of the outrigger 98 that faces the skin of the patient. If the side of the outrigger 98 is between marks, the smaller dimension which is hidden inside the support end 114 is used. Conversely, if the marking 118 is flush with the side of the support end 114, that dimension is selected.

Once the drill guide 94 is appropriately positioned as described above, a drill-tipped K-wire is drilled through the aiming bullet 110 according to known techniques until it stops against the lateral side of the insertion rod 96. Once this transverse bore is made, the drill guide 94 is disassembled by reversal of the above-identified steps, and is removed. The femoral tunnel 28 is thereafter visualized by advancing and rotating an arthroscope through a portal made at the junction of the central and lateral third of the patella tendon (not shown).

The K-wire, left in place after removal of the components of the drill guide 94, is then gently tapped across the femoral tunnel 28 about 5 to 10 mm into the medial wall with a mallet (not shown). The K-wire is properly positioned when it is within one millimeter of bisecting the femoral tunnel 28. In the event that the K-wire is not properly centered, the transverse bore is redrilled.

With reference to FIG. 10, once the initial bore for the transverse femoral tunnel 26 is properly drilled, a reamer 124 having an axial throughbore and a drill sleeve (not shown) for placement around the reamer 124 are selected according to size to drill over the K-wire to form the transverse tunnel 26 as illustrated in FIG. 10. The drill sleeve is used to catch the bone reamings, or mulch. The reamer 124 should be drilled across the width of the femoral tunnel 28, but not into the medial wall.

Thereafter, a motorized shaver (not shown) is inserted through the transverse tunnel 26 to vacuum bone debris from the femoral tunnel 28. An impingement rod (also not shown) is advanced through the transverse tunnel 26 and across the femoral tunnel 28 to ensure centering of the tunnel. The impingement rod is then removed. Approximately 1 to 2 millimeters of bone is removed from the anterior and posterior walls of the femoral tunnel 28 by manipulating an angled curette through the transverse tunnel 26.

The outer screw 42 is thereafter inserted into the transverse tunnel 26 as illustrated in FIG. 11 by means of a tool such as screwdriver 126 preferably having a hexagonal configuration as illustrated. The screw 42 is inserted so that the opening 68 of the screw 42 is in line with the groove on the screwdriver 126, thus allowing the surgeon to later verify that the position of the opening 68 is faced downward toward the open end of the femoral tunnel 28. The screw 42 is partially inserted so that its nose 48 is approximately two-thirds across the femoral tunnel 28.

Once the outer screw 42 is in the position as described above, a monofilament suture 128, as shown in FIG. 11, is looped through a hollow elongated suture passing device 130. The device 130 is maneuvered through the tibial tunnel 32 into the femoral tunnel 28 and positioned so that the a loop 132 is located around the nose 48 of the outer screw 42. The screw 42 is next advanced through the transverse tunnel 26 so that the nose 48 is positioned completely across the femoral blind bore thus embedding approximately 2–3 mm of the tip of the nose 48 into the medial wall of the femoral tunnel 28. Advancement of the screw 42 is halted when the nose 48 is embedded and the groove on a screw driver is facing the intercondylar notch 108 as illustrated in FIG. 12.

The suture passing device 130 is then removed with take being taken not to twist the suture 128. Twisting of the suture will cause the graft bundle 22 to tangle and will prevent its smooth passage.

The tapered ends 36 and 38 of each of the two individual grafts of the graft bundle 22 are selected and a posterior limb of the passing suture is tied to the two whip stitches (shown above in FIG. 4b). Thereafter the untied end of the passing suture 128 is pulled through the tibial tunnel 32, into the femoral tunnel 28, around the nose 48 of the outer screw 42, out of the femoral tunnel 28, and back through the tibial tunnel 32 thus allowing the graft to pass through the same path. The passing suture 128 is removed and the ends 36, 36', 38, and 38' of the graft bundle 22 are evened out.

It is desirable that constant firm tension be applied to the free end of the suture 128 during the pulling process such that both tendons comprising the graft bundle 22 are pulled at the same rate through the tunnels and around the nose 48. If either individual tendon or the graft bundle 22 hangs up, it will be necessary to back out both grafts out a few centimeters and then pull the wider semitendinosus graft through first and follow with the narrower, gracilis graft. Again, in this event, the position of each graft is adjusted until each limb extending out of the tibial tunnel 32 is equal.

The next step is to mechanically fix the graft bundle 22 in its proper position. The first step of the fixing procedure is to check the graft excursion profile by removing irrigation fluid, hyperextending the knee and simultaneously grasping the quartet of graft ends 34 at their exit from the tibial tunnel 32. A constant tension is applied and the knee is slowly flexed. Typically, the graft bundle 22 will move 0 to 2 millimeters out of the tibial tunnel 32 with knee flexion. This is an acceptable excursion profile. The graft bundle 22 is next secured to the tibial cortex by a fastener such as fastener 40 shown above with respect to FIG. 1 and also shown in FIG. 12. The fastener 40 may be a screw and washer or other ligament fixation device. The graft bundle 22 is secured to the tibial cortex with the fastener 40 while applying tension to all four tendon ends with the knee in full extension. The surgeon thereafter inserts the arthroscope and the tension on the graft bundle 22 is next examined.

As noted above, the present invention provides a system by which the long-term bond between the tendon grafts and the femoral tunnel 28 can be augmented. This is accomplished by providing the opportunity for a biologic bond to be formed between the hamstring graft and the walls of the femoral tunnel 28. The bone mulch that was collected from the bone reaming steps described above is inserted into the femoral tunnel 28 through the throughbore 66 of the outer screw 42 fitted within the transverse tunnel 26. This step is accomplished by inserting a bone graft delivery sleeve 134 illustrated in FIG. 13 into the matching hex of the end 52 of the outer screw 42. It will be appreciated that other materials which induce biological bonding materials may also be used as a substitute for bone mulch. Such biological bonding materials include, but are not limited to tricalcium phosphate, hydroxyapatite, bone reamings and other suitable materials.

Once the sleeve 134 is positioned at the end 52 of the screw 42, a bone graft impactor 136 is inserted through the sleeve 134 and into the throughbore 66 of the screw 42. The impactor 136 includes an elongated shaft 138 having a conically-shaped impacting end 140 and a handle 142. The conically-shaped impacting end 140 is formed to nest with the concave wall 64 formed at the end of the throughbore 66. The elongated shaft 138 has defined thereon a plurality of adjacent peripheral markings 144.

With the impactor 136 positioned within both the sleeve 134 and the screw 42, the impactor 136 is advanced into the throughbore 66 until it stops against the wall 64. Thereafter, the marks on the inner screw 44 are examined at an opening 152 defined in the delivery sleeve 134. The impactor 136 is fully seated when the marking on the inner screw 44 matches the length of the outer screw 42.

The impactor 136 is then withdrawn from the sleeve 134 and bone mulch is sprinkled into the slot 152 on the delivery sleeve 134. The bone graft impactor 136 is then reinserted into the delivery sleeve 134 and is driven through the outer screw 42 and into the femoral blind bore 16 by gently tapping the handle 142 of the impactor 136 with a mallet (not shown) until the impactor 136 bottoms out at the base of the screw 42. This step is repeated until all of the bone graft is used. Verification that the throughbore 66 of the outer screw 42 has been completely emptied of bone graft is made by confirming that the bone graft impactor 136 has been fully seated inside the bone mulch screw by cross checking the depth previously identified before mulch was placed within the screw 42.

Once proper seating of the end of the impactor 154 is verified, the impactor 136 is removed from the sleeve 134, and the sleeve 134 itself is removed from the end of the outer screw 42. Finally, and with respect to FIG. 14, the reverse-threaded, inner screw 44 is inserted into the outer screw 42 by a conventional tool such as a hex screw driver 146 of a conventional size. The inner screw 44 fully seats against the seat 70 of the bore 66 after approximately 4 or 5 turns. It is important to discontinue turning of the inner screw 44 once it is seated otherwise the turning of the screw 44 will result in the outer screw 42 being withdrawn from the femur 12. This latter arrangement, while allowing for subsequent removal of the screw assembly 24 by a conventional type of screwdriver from the femur 12 at a future time when the graft is bonded, is not desirable until healing has occurred. It will also be noted that by allowing inner screw 44 to seat within the outer screw 44, the bore 66 which is used to receive bone mulch can be relatively large. Nevertheless, the two-part screw assembly 24 can be removed using a relatively small conventional screwdriver because the screw driver needs only to engage the inner screw 44.

Having described the invention, however, many modifications thereto will become apparent to those skilled in the art to which it pertains. For example, the two part screw assembly may be made from a resorbable material. Accordingly, other modifications can be made without deviation from the spirit of the invention as defined by the scope of the appended claims.

What is claimed is:

1. An apparatus for securing a portion of a graft to a femur, said femur having a tunnel, said apparatus comprising:

a first end;
   a second end;
   an intermediate portion being positioned between said first end and said second end; and
   means for allowing bone mulch to pass at least partially through said intermediate portion between said firm end and said second end,
   an exterior opening disposed between said first end and said second end being in communication with said means for allowing said bone mulch to pass,
   whereby the bone mulch can be disposed in a region of said femoral tunnel proximate to the graft.

2. The apparatus for securing a portion of a graft set forth in claim 1, wherein said means for allowing the biological bonding material to pass through said intermediate portion includes a passage, said passage being substantially continuous from a region of said apparatus proximate to said first end to a region of said apparatus proximate to said second end.

3. The apparatus for securing a portion of a graft set forth in claim 2, further comprising means for driving the biological bonding material through said passage.

4. The apparatus for securing a portion of a graft set forth in claim 1, wherein said intermediate portion has threads formed thereon, said threads being operable to engage the femur.

5. The apparatus for securing a portion of a graft set forth in claim 4, wherein said first end, said second end, and said intermediate portion define an outer member, said apparatus further including an inner member, said inner member being selectively positionable within said means for allowing bone mulch material to pass out of said outer member.

6. The apparatus for securing a portion of a graft set forth in claim 5, wherein said means for allowing the bone mulch material to pass defines an axial bore for receiving said inner member, said inner member further includes an outer thread and said axial bore of said outer member has an inner thread, said outer thread and said inner thread being operatively mateable.

7. The apparatus for securing a portion of a graft set forth in claim 6, wherein the orientation of said outer thread on said inner member and the orientation of the inner thread on said axial bore is in opposite helical orientation of said threads on said intermediate portion.

8. An apparatus for securing a portion of a graft within a tunnel formed in a femur, both mechanically and by introduction of bone mulch into the tunnel, comprising:

a proximal end;
   a distal end;
   a threaded proximal portion having an entry opening formed therein, said entry opening being operable to receive the bone mulch therein;
   a substantially smooth portion for mechanically engaging the graft; and
   an exterior opening disposed between said proximal and distal ends being in communication with said entry opening,
   whereby the bone mulch may be introduced into the tunnel through said exterior opening to enhance fixation of the graft within the tunnel.

9. The apparatus for securing a portion of a tendon graft set forth in claim 8, further comprising a passage formed between said entry opening and said exterior opening.

10. The apparatus for securing a portion of a tendon graft set forth in claim 9, further comprising means for driving the bone mulch material through said passage.

11. The apparatus for securing a portion of a tendon graft set forth in claim 10, wherein said means for driving the bone mulch material is an inner member selectively positionable within said passage.

12. The apparatus for securing a portion of a tendon graft set forth in claim 11, wherein said inner member includes an outer thread and said passage has an inner thread, said outer thread and said inner thread being operatively mateable.

13. The apparatus for securing a portion of a tendon graft set forth in claim 12, wherein the orientation of said outer thread on said inner member and the orientation of the inner thread of said passage is in opposite helical orientation of said threads on said threaded proximal portion.

14. An apparatus for securing a portion of a graft to a femur, said femur having a tunnel, said apparatus comprising:

a first end;
   a second end;
   an intermediate portion being positioned between said first end and said second end, said intermediate portion having threads formed thereon, said threads being operable to engage the femur, said first end, said second end, and said intermediate portion defining an outer member;
   an inner member being selectively positionable within said means for allowing biological bonding material to pass out of said outer member;
   means for allowing a biological bonding material to pass at least partially through said intermediate portion between said first end and said second end; and
   an exterior opening disposed between said first end and said second end being in communication with said means for allowing a biological bonding material to pass,
   whereby the biological bonding material can be disposed in a region of said femoral tunnel proximate to the graft.

15. The apparatus of claim 14, wherein said means for allowing the biological bonding material to pass defines an axial bore for receiving said inner member, said inner member further including an outer thread and said axial bore of said outer member having an inner thread, said outer thread and said inner thread being operatively mateable.

16. The apparatus of claim 15, wherein the orientation of said outer thread on said inner member and the orientation of the inner thread on said axial bore is in opposite helical orientation of said threads on said intermediate portion.

17. An apparatus for securing a portion of a graft within a tunnel formed in a bone, both mechanically and by introduction of a biological material into the tunnel, comprising:

a proximal end;

a distal end;

a threaded proximal portion having an entry opening formed therein into which the biological material may be introduced;

a substantially smooth portion for mechanically engaging the graft; and an exterior opening disposed between said proximal and distal ends being in communication with said entry opening;

a passage formed between said entry opening and said exterior opening;

an inner member selectively positionable within said passage, said inner member including an outer thread and said passage having an inner thread, said outer thread and said inner thread being operatively mateable, whereby the biological material may be introduced into the tunnel through said exterior opening to enhance fixation of the graft within the tunnel.

18. The apparatus of claim 17, wherein the orientation of said outer thread on said inner member and the orientation of the inner thread of said passage is in opposite helical orientation of said threads on said threaded proximal portion.

* * * * *

UNITED STATES PATENT AND TRADEMARK OFFICE
CERTIFICATE OF CORRECTION

PATENT NO. : 5,674,224

DATED : October 7, 1997

INVENTOR(S) : Stephen M. Howell, et al.

It is certified that error appears in the above-identified patent and that said Letters Patent is hereby corrected as shown below:

Column 7, line 19, delete "the a" and insert --a--.
Column 8, line 67, "44" should be --42--.
Column 9, line 20, Claim 1, "firm" should be --first--.
Column 9, line 46, Claim 5, delete "material" after --mulch--.
Column 9, line 49, Claim 6, delete "material" after --mulch--.
Column 10, line 14, Claim 10, delete "material" after --mulch--.
Column 10, line 18, Claim 11, delete "material" after --mulch--.

Signed and Sealed this

Second Day of February, 1999

Attest:

Attesting Officer

Acting Commissioner of Patents and Trademarks